United States Patent [19]

Voegele et al.

[11] 4,411,220
[45] Oct. 25, 1983

[54] MASS PRODUCTION UNIT FOR PRODUCING EGGS OF AN INSECT

[75] Inventors: Jean D. Voegele; Pierre E. J. Jourdheuil, both of Antibes; Jeanne Daumal, Juan-les-Pins, all of France

[73] Assignee: Inst. Nat. de la Recherche Agronomique, France

[21] Appl. No.: 243,961

[22] PCT Filed: Jul. 7, 1980

[86] PCT No.: PCT/FR80/00113
§ 371 Date: Mar. 6, 1981
§ 102(e) Date: Mar. 6, 1981

[87] PCT Pub. No.: WO81/00185
PCT Pub. Date: Feb. 5, 1981

[30] Foreign Application Priority Data

Jul. 10, 1979 [FR] France ............................ 79 17904

[51] Int. Cl.³ .............................................. A01K 67/00
[52] U.S. Cl. .......................................... 119/1; 119/15
[58] Field of Search ............................... 119/1, 15

[56] References Cited

U.S. PATENT DOCUMENTS

| | | | |
|---|---|---|---|
| 2,539,633 | 1/1951 | Morrill | 119/1 |
| 3,847,113 | 11/1974 | Andreev et al. | 119/1 X |
| 3,893,420 | 7/1975 | Andreev et al. | 119/1 |
| 3,941,089 | 3/1976 | Andreev et al. | 119/1 |
| 4,106,438 | 8/1978 | Nelson | 119/1 |

Primary Examiner—Hugh R. Chamblee
Attorney, Agent, or Firm—Karl W. Flocks; Sheridan Neimark

[57] ABSTRACT

Such production unit comprises namely an incubator (1) with ventilated housing comprising horizontal alveoli elements, a hatchery (2) containing said alveoli elements arranged vertically and provided with an inlet of carbonic acid gas, a laying place (5) comprising an arrangement of vertical thin plates at right angles with an outlet hopper towards a collecting member (6) and pneumatic transport conduits (7,8). Application to the production of eggs of the meal pyralis genus, intended to be used as substitution host particularly for trichogrammidae.

7 Claims, 6 Drawing Figures

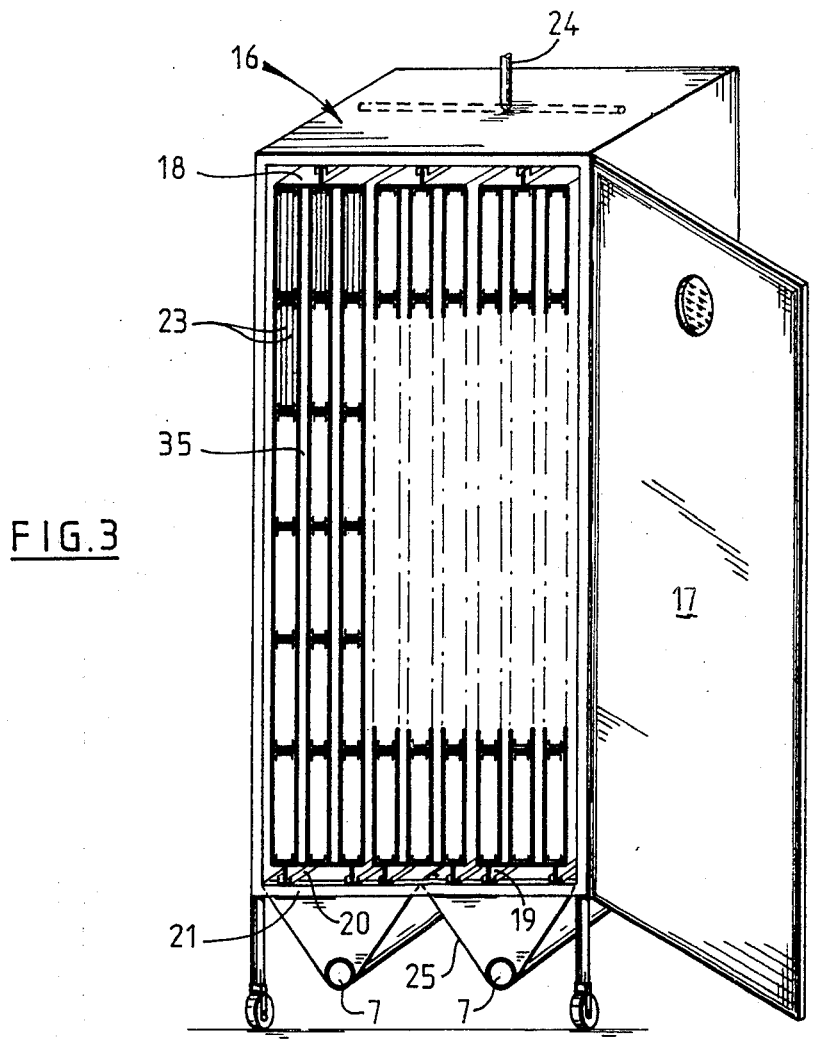
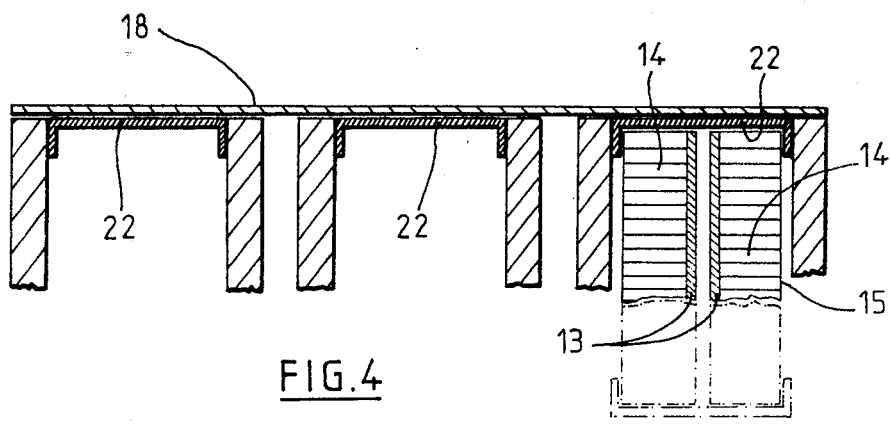

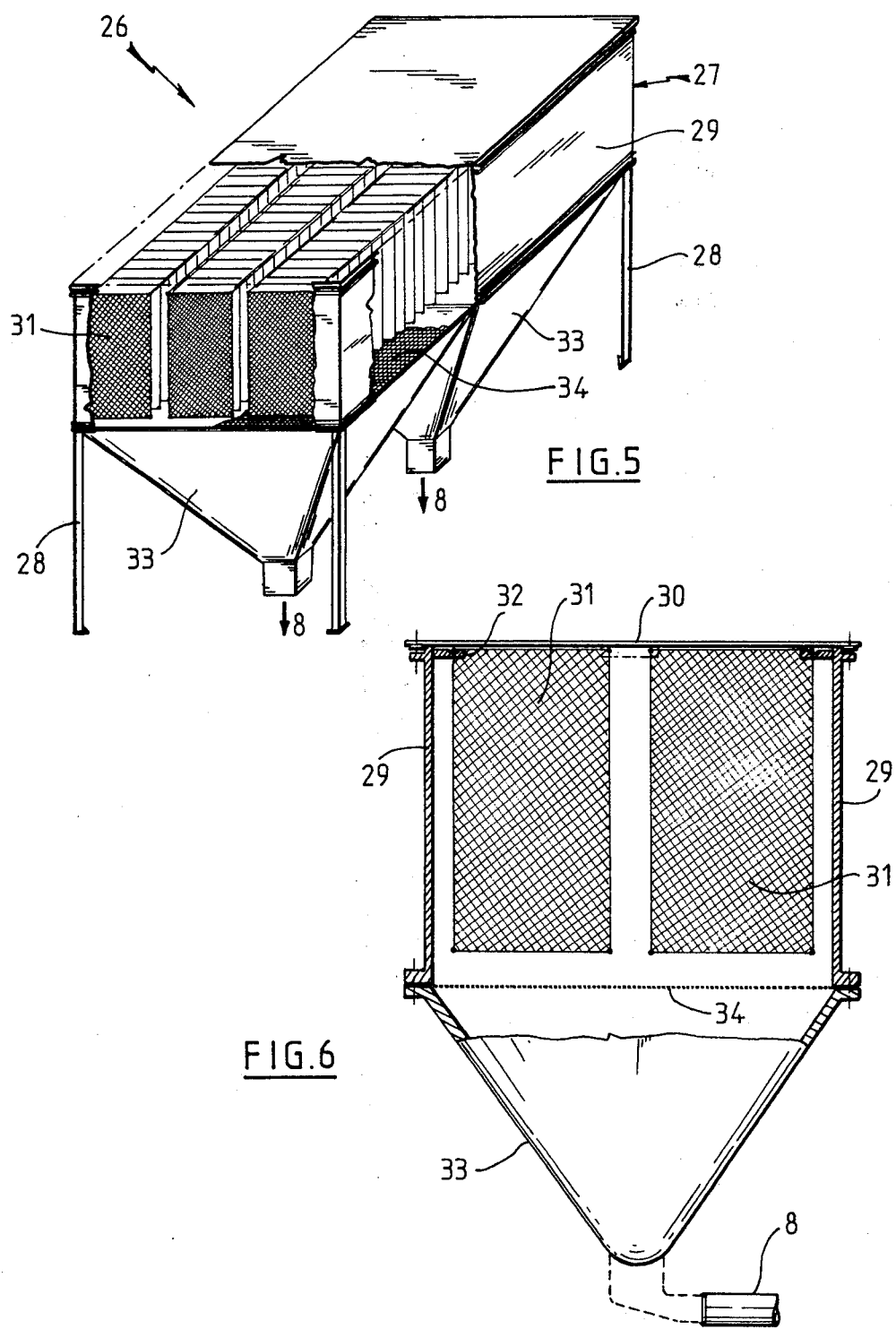

MASS PRODUCTION UNIT FOR PRODUCING EGGS OF AN INSECT

BACKGROUND OF THE INVENTION

The present invention relates to a mass-production unit for eggs of an insect. It is known that, in the field of agriculture and more precisely the protection of plants by the biological route against damaging insects, it is possible to apply various predator or parasite Entomophages, such as Trichogramma, and that it is possible to obtain them by passing through a substitute host such as the egg of pyralis of flour (flour-moth).

The present invention therefore relates to a mass-production unit for eggs of this substitute host.

DESCRIPTION OF THE PRIOR ART

The raising of the pyralis of flour, in particular of Ephestia kuhniella, on the laboratory scale, has been described by Daumal and Collaborators (1975). In accordance with the method described, there is dispersed on the bottom of closed compartments hard wheat semolina, then a panel of corrugated cardboard including a certain number of elemental cells or alveoles. An inoculum of eggs of the meal-moth is spread on the bottom of the cover of the compartment. After hatching, the caterpillars are allowed to fall on to the cardboard, they utilize the semolina and form nymphs in the cells after a development of 45 days at a temperature between 12° and 25° C. This thermoperiod includes low temperatures which avoid sudden heating within development compartments as well as, consequently, epizootics. At the beginning of the appearance of the adults, the panels are brushed and then introduced into a hatcher where the adults emerge over a span of 20 to 30 days. These adult individuals are recovered daily by the pneumatic route after narcosis with carbon dioxide. They are then transferred by the same route into laying places of a transparent plastic material including rows of rods also plastics material serving as a support for the eggs laid by the adults. The eggs then fall through a grid which lies the bottom of these laying places onto a conveyer belt which leads them to a scrubber where they are freed from the moth scales with which they are associated.

This breeding method has a certain number of drawbacks among which are notably: too numerous manipulations, occupation of too large surfaces and of too large volumes, competition of the caterpillars, difficulty of checking temperatures within compartments, eggs laid by adults with considerable loss of eggs on corpses, expense of carbon dioxide, loss of cardboard pannels on each generation, etc.

The production unit according to the invention enables the drawbacks to be overcome by applying the discoveries of Applicant to the behaviour of the pyralis of flour:

(1) The pyralis caterpiller weaves constantly a territorial marking thread which agglomerates the food particles encountered in its path and it is endowed with a negative geotaxy. It perceives in particular the light indication and aerated open media (aerotaxy). In the case of a favorable medium, it forms a cocoon very precociously where the emergence site of the imago is already provided and materialised, well before nymphosis, by a hole that it forms on the side of the open or aerated medium, the layer being constitutable by a fine membrane permeable to air separating the cocoon from the open medium. This behaviour hence enables three quite reliable breeding modalities to be contemplated, according as the food is alone, situated in a housing by the caterpillar or at the side of such a housing. The first modality appears the simplest, the exit indicator being given by the meshes of a grid and the caterpillar fabricating its housing. However, the following modalities appear preferable and resort to housings combined into alveoled frames as will be explained in detail below.

(2) The meal-moth caterpillar develops more easily in vertical chambers in a semolina which has already reached a certain granulation and called "fine seeding" in the milling trade, which corresponds to an average granulometry of 346 microns. The optimum food ration is 0.2 g per caterpillar, a ration of 0.13 to 0.15 g being however very suitable.

(3) Relatively low temperatures, of the order of 10° C., enable, after the embryonic development and the beginning of the first larval stage at 20° C., a slow development for 5 months which ends in the pre-nymph stage, which stage must not be exceeded at this temperature at the risk of sterilising the males. The larval population can at any moment be replaced at 20° C. for obtaining nymphosis and the emergence of the adults, which takes place in a period of 20 days. This preservation in the cold favours on the one hand the occlusion of the alveolae by the secretion of a plug of silk by the caterpillars, with also a better occupation of the alveolae leading to the production of a number of adults corresponding to a yield three times greater approximately than that described in the known breeding method and, on the other hand, after passage of the caterpillars at 20° C. or at any other development resumption temperature, to a regrouping of the emergences with a fertility which can practically double. This grouping of the emergences is effected in fact in 15 days instead of 30 days at 20° C. in the case of the rearing method mentioned above. The final yield thus obtained is hence six times greater approximately than that previously described, under considerably improved conditions of safety and flexibility. Applicant has in fact discovered in addition that the development in the cold presents the advantage of avoiding the installation of epizootics of the Mattesia dispora type for example. However, the pre-adult development could be carried out at a rapid growth temperature comprised between 20° and 23° C. for example, having the advantage of more rapid occupation of the sites and of a higher cumulative production in one year.

(4) The very heterogeneous development of a population from Ephestia kuhniella eggs can be considerably regularised by very considerable mixing with air.

DESCRIPTION OF THE INVENTION

In accordance with the invention, a mass-production unit for the eggs of an insect, notably of the flour meal-moth genus, of the type comprising an incubator including cellular elements, a hatcher and a laying place, includes an incubator constituted by a ventilated enclosure containing movable supports for stacks of cellular plates or bins of cellular frames arranged in their horizontal plane, a hatcher designed to contain movable supports for stacks of said plates parallel and edge-wise, in line with an exit hopper and provided with a carbon dioxide inlet, and a laying place including an arrangement of parallel sheets positioned edge-wise in line with an outlet hopper directed to a collecting member, the hatcher, the laying place and the collector being connected successively by a pneumatic transporting duct, the incubator, the hatcher and the laying place being in addition provided with members for temperature regulation and, if necessary, ventilation regulation.

According to other features:

Each cellular plate is constituted by a mat with a rigid planar base provided with cavities arranged perpendicularly to said base and open at the end opposite the latter; each cellular frame is constituted by the same mat open at the two solid surfaces;

Each movable stack support of the incubator is constituted by a carriage provided with holding members designed to form a regular space between the plates or the bins of frames;

The hatcher is constituted by a hermetically closed container and it comprises sliding drawers designed to contain groups of two plates on edge coupled through their base, with regular spacing between the faces of the open ends of the alveoles or cells, a carbon dioxide inlet at the upper part, a ventilator and at least one hopper at its lower part connected by a pneumatic transport duct to the entrance of the ovipositor;

The laying place is constituted by a container including supports intended for the arrangement of sheets edge-wise parallel with one another with regular spacing between said sheets, the latter being arranged above a sifting grid itself arranged in line with at least one outlet hopper connected through a pneumatic transport duct to the inlet of the collector.

The collector can comprise a conveyor belt itself connectable to a scrubber for removing waste associated with the eggs collected.

BRIEF DESCRIPTION OF THE DRAWINGS

Other characteristics and advantages of the invention will emerge better from the description which follows, made with regard to the accompanying drawings in which:

FIG. 3 shows a diagrammatic perspective view of a hatcher fitted with its mat supports;

FIG. 4 shows a detail of a support of the hatcher according to FIG. 3;

FIG. 5 shows a diagrammatic view in perspective of a laying place fitted with its sheets; and FIG. 6 shows a diagrammatic view in cross-section of the laying place of FIG. 5.

In these drawings, the same reference numerals denote the same elements.

BEST MANNER OF CARRYING OUT THE INVENTION

Figure 1:
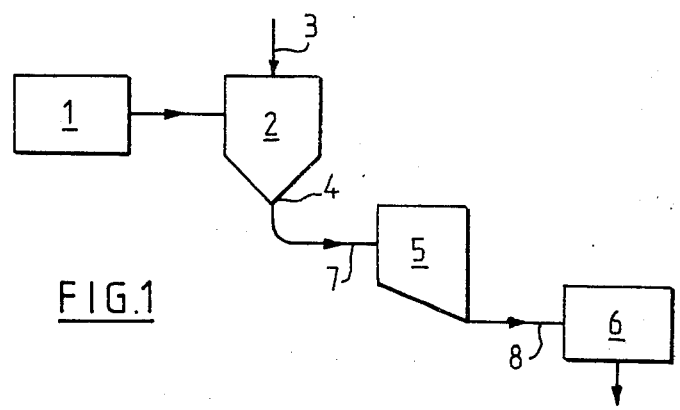
FIG. 1 shows a block diagram of a production unit according to the invention.

Referring to FIG. 1, the production unit according to the invention comprises essentially an incubator 1 containing either mats or bins of which each alveole or cell is occupied by a larva or by an egg, a hatcher 2 provided at its upper part with carbon dioxide inlet 3 connected through its necked lower part 4 to a laying place 5 whose bottom is itself inclined into a neck and connected to a station or to a collector member 6. It should be noted that, in accordance with the invention, the only manual operation necessary resides in the extraction of the mats from the incubator 1 and their introduction into the hatcher 2. The other transfers take place respectively through pneumatic transport ducts 7 and 8 up to the collector.

Figure 2:
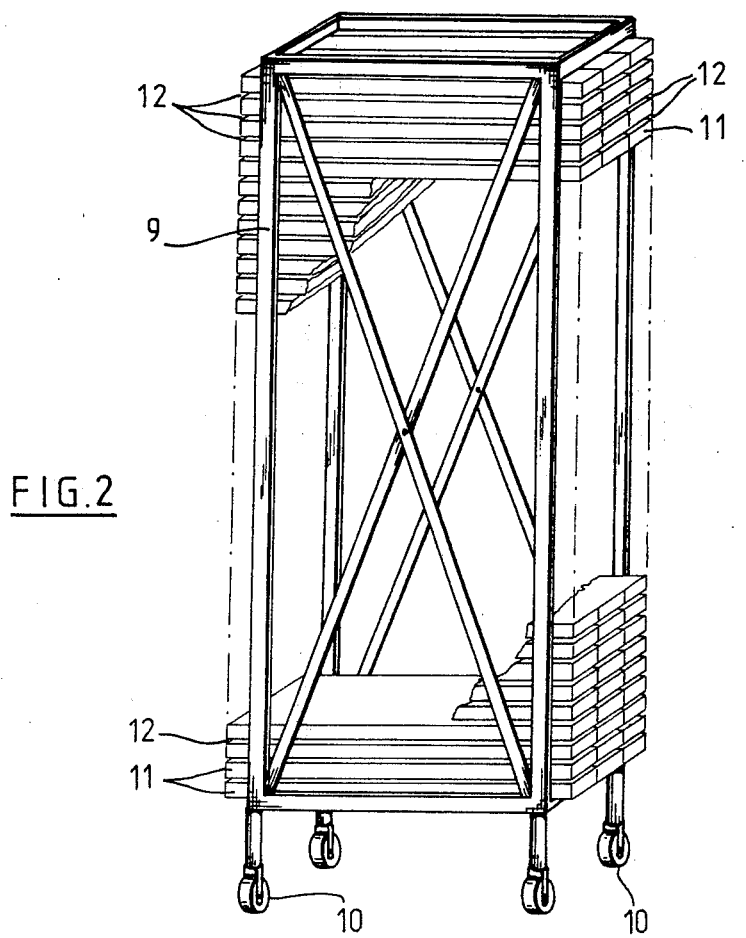
FIG. 2 shows a diagrammatic perspective view of a plate support of the incubator.

Referring to FIG. 2, a movable support for stacking plates from the incubator 1 is constituted by a cart comprising a frame, for example of metal 9 mounted on feet which can themselves be provided with suitable castors 10. This cart is provided with suitable holding members designed to effect a stacking of the plates 11 arranged parallel with one another bearing on their base with regular spacing 12.

Each cellular plate or alveolar frame is constituted by a flat base 13 closed by the plate and open for the frame (see FIG. 4) provided with cells 14 arranged perpendicular to said base and comprising an open end 15. These mats can be pre-fabricated and formed for example of massicoted cardboard or of a smooth and washable plastics material, which permits reutilisation and easy maintenance.

Referring to FIG. 3, the hatcher is constituted by a container 16 provided with a door 17 which can ensure a pneumatic closing and it comprises slide drawers 18 the lower part of each of which is provided with rails 19 which can slide in tracks 20 themselves bearing on the lower portion of a frame 21.

Each drawer 18 is constitutd by rigid frame provided for example with angle bars 22 designed for holding groups of two mats coupled back to back through their respectives bases 13. As mentioned above, the groups of two mats 23 are arranged edge-wise.

At the upper portion of the enclosure 16 of the hatcher is arranged a suitable duct 24 for the introduction of carbon dioxide, as will be explained in more detail below. The lower portion of the hatcher 16 is provided with at least one bottom with walls inclined into a hopper 25 of which the lower portion is connected to the pneumatic transport duct 7. Advantageously, the hatcher also includes a lower ventilator of any suitable type (not shown).

Referring to FIGS. 5 and 6, a laying place 26 according to the invention is constituted for example by an enclosure, of which the upper portion 27 is parallelepipedic, and provided with feet 28. The parallelepipedic upper portion comprises lateral walls 29 at the upper part of which they can be mounted in a removable cover 30. Sheets 31 are mounted edge-wide parallel with one another, with regular spacing between them, and can be for example suspended from the cover 30 or through supports and suitable angle bars 32. The parallelepipedic enclosure 27 is mounted by means of the lower portion of the wall 29 in line with a hopper or gutter 33, a grid 24 being interposed between the lower portion of the sheets 31 and the entrance of the neck 33. The lower portion of the neck 33 is connected to the pneumatic suction duct 8. The grid 34 has notably the purpose of carrying out a first sifting of the eggs produced and becoming detached from the sheets 31, whilst the duct 8 leads the eggs produced, if necessary associated with various waste to a scrubber (not shown), by, for example, a conveyor belt. The possibility of dismounting the cover 30 and the parallelepipedic portion 27, as well as the grid 34, enables cleaning and easy maintenance of the laying place 26, as well as the arrangement of the parallelelpipedic assembly on a caisson open at the upper portion in which a conveyor belt transports the eggs and the scales to the scrubber. In this case, each parallelepipedic assembly is pierced by two holes, one for the entrance of the imagos, the other for the continuous and powerful suction of the scales. In addition, each assembly is provided under the grid 34 with a sealing plate to ensure the necessary suction for the aspiration of the adults through the pneumatic duct. Such laying places permit, with respect to known laying places, increased fertility and longevity, for an occupied space 3.5 times smaller.

For putting into operation the production unit according to the invention, the alveoles 14 of the mats 1 are filled with semolina in the required amount, either manually, or by automatic distributors. The eggs are distributed on the semolina with an excipient of the same semolina, the latter being then sprayed in the presence of water, in the proportion of one egg per cell, namely by dusting. It is possible to carry out this distribution by sanders or through the pneumatic duct by means of a suction box pierced with holes of diameter less than that of the egg and spaced in the proportion of one hole per cell, the caterpillars distributing themselves in the spaces available. As mentioned above, the temperature of the incubator 1, which can be an enclosure or a ventilated room, is kept between 10° and 20° C. for the time necessary for the embryonic development up to the pre-nymph stage.

At this stage, the mats are taken out of the incubator and introduced in the arrangement indicated into the hatcher 2. The latter is lept at the temperature favorable for hatching during the time required to obtain moth capable of laying. At this stage, narcosis of the imagos is carried out by means of carbon dioxide introduced through the pipe 24. Applicant has noted that a flow rate of 3 l of carbon dioxide at 2 bars pressure in 160 seconds suffices to produce narcosis of the imagos which fall down the passages 35 (FIG. 3) formed between the groups of mats 23. Applicant has however found that it is possible to reduce the consumption of carbon dioxide mentioned above 10 times by lowering for about one hour the temperature of the hatcher to 10°-11° C. The narcosised moth are then transferred pneumatically through the duct 7 into the laying place 26, from whence the eggs are then extracted by aspiration as described above.

POSSIBILITIES OF INDUSTRIAL APPLICATION

By way of example, it is possible to produce cellular plates or alveolar frames including 18000 cells of 70 cm by 27 cm, that is to say with a surface of 1890 cm 2. According to the prior method of Daumal limited to 75000 lodgements, it was possible to obtain 5250 adults whereas according to the present invention, it is possible to obtain 13600 adults per 18400 alveoles, that is to say a yield of 2.4 times greater, whilst benefiting from the compactness and convenience of operation which can, besides, be suitably automatised. In accordance with the invention, the consumption of semolina to obtain this number of adults is respectively 3.6 kg, 2.7 kg and 2 kg for respective food rations of 0.2 g, 0.15 g and 0.13 g per caterpillar. With stacks of three bins or alveolar plates including therein a spacing of 1 cm, there is obtained, per cart of the type shown in FIG. 2, a stack height of 198 cm, giving 1,468,000 adults for the bins and substantially 2,000,000 for the alveolar plates, this for a ground area of 0.6 m2. If account is taken of a sex-ratio 1/1 and an average fertility of 200 eggs per female, a regular production of 150 to 200 millions eggs is obtained.

The hatcher may be of variable dimensions, for example with a content of 108 units of 0.8 by 0.75 m, the groups of two superposed mats being stackable in nine vertical planes spaced from one another by a passage (35) of 3 cm. It should however be noted that the hatcher can be provided to contain mat supports arranged not edge-wise but horizontally and parallel to one another.

It is well understood that the present invention has only been described and shown by way of explanation and not in any limiting manner and that it would be possible to introduce any modification therein within the field of technical equivalents without departing from its scope.

1. Mass-production unit for the eggs of an insect, notably of the meal-moth genus, comprising:
   an incubator for eggs of said insect, including a ventilated enclosure comprising movable supports for stacks of alveolar elements horizontally, said alveolar elements each containing one egg and a dosed amount of feeding semolia;
   a hatcher for receiving eggs at the pre-nymph stage from said incubator and containing movable supports for the stacking of said alveolar elements in parallel and edge-wise in line with an outlet hopper, and provided with a carbon dioxide inlet for the narcosis of imagos emerging from said pre-nymph stage; and
   a laying place wherein said imagos provide for the production of eggs, including an arrangement of parallel sheets arranged edge-wise in line with an outlet hopper to a collector member for said eggs;
   said hatcher, laying place and collector being connected successively by a pneumatic transport duct, said incubator, hatcher and laying place being provided with means for regulating temperature and, if necessary, ventilation 2. Production unit according to claim 1, wherein the alveolar elements are constituted by plates with a rigid flat base provided with alveoles arranged perpendicularly to said base and open at the end opposite the latter.

3. Production unit according to claim 1, wherein the alveolar elements are constituted by bins with alveolar frames.

4. Production unit according to claim 1, wherein each movable stack support of the incubator is constituted by a cart provided with holding members designed to form a regular spacing between said alveolar elements.

5. Production unit according to claim 1, wherein the hatcher is constituted by a container with hermetic closing and comprises drawers with slides designed to contain groups of two plates edge-wise coupled through their base, with regular spacing between the surfaces of the open ends of the alveoles, a ventilator and at least one hopper at its lower portion connected by a pneumatic transport duct to the entrance of the ovipositor.

6. Production unit according to claim 1, in which the laying place is constituted by an enclosure comprising a continuous and powerful aspiration of the scales and supports designed for the arrangement of the sheets edge-wise parallel with one another with regular spacing between said sheets the latter being arranged above a sifting grid itself arranged in line with at least one outlet hopper connected by a pneumatic transport duct to the entrance of the collector.

7. Production unit according to claim 1, wherein the collector comprises a conveyor belt itself connectable with a scrubber for removing scraps associated with the collected eggs.

* * * * *